(12) United States Patent
Bommarito

(10) Patent No.: US 7,763,289 B2
(45) Date of Patent: Jul. 27, 2010

(54) TOPICAL TURMERIC SKIN CARE PRODUCTS

(75) Inventor: Alexander A. Bommarito, Freeland, MI (US)

(73) Assignee: JoAl's Products, LLC, Saginaw, MI (US)

( * ) Notice: Subject to any disclaimer, the term of this patent is extended or adjusted under 35 U.S.C. 154(b) by 0 days.

(21) Appl. No.: 12/148,242

(22) Filed: Apr. 17, 2008

(65) Prior Publication Data

US 2009/0208431 A1 Aug. 20, 2009

Related U.S. Application Data

(63) Continuation-in-part of application No. 11/509,212, filed on Aug. 24, 2006, now abandoned.

(60) Provisional application No. 60/713,560, filed on Sep. 1, 2005.

(51) Int. Cl.
*A61K 36/00* (2006.01)
*A61K 36/906* (2006.01)
*A61K 36/45* (2006.01)
*A61K 36/87* (2006.01)

(52) U.S. Cl. .................. 424/725; 424/756; 424/732; 424/773; 424/777; 424/766

(58) Field of Classification Search .................. None
See application file for complete search history.

(56) References Cited

U.S. PATENT DOCUMENTS

| | | | |
|---|---|---|---|
| 5,674,912 A | 10/1997 | Martin | |
| 5,897,865 A | 4/1999 | Nguyen | |
| 6,048,533 A | 4/2000 | Nguyen | |
| 6,074,630 A | 6/2000 | DeVillez et al. | |
| 6,153,208 A | 11/2000 | McAtee et al. | |
| 6,231,837 B1 | 5/2001 | Stroud et al. | |
| 2003/0113388 A1 | 6/2003 | Phan | |
| 2003/0228268 A1 | 12/2003 | Candau | |
| 2004/0076691 A1* | 4/2004 | Haines et al. | 424/729 |
| 2005/0084551 A1 | 4/2005 | Jensen et al. | |
| 2005/0123632 A1 | 6/2005 | Chen et al. | |
| 2005/0191267 A1* | 9/2005 | Luanratana | 424/74 |

FOREIGN PATENT DOCUMENTS

KR 2001077652 A * 8/2001

OTHER PUBLICATIONS 1 page article from Mewscape, 10th Anniversary, www.medscape.com/viewarticle/494252, 2004.
Antioxidant Curcuma Extracts Decrease the Blood Lipid Peroxide Levels of Human Subjects (AGE), vol. 1, pp. 167-169, 1995.
www.turmeric-curcumin.com/curcumin.html Turmeric-Curcumin.Com pp. 1-14, Aug. 10, 2005.
J Pharm Pharmaceut Sci (www.ualberta.ca/-csps) Comparative effects of curcumin and an analog of curcumin on alcohol and PUFA induced oxidative stress—Rajagopalan Rukkumani, Kode Aruna, Penumathsa Suresh Varma, Kallikat Narayanan Rajasekaran, Venugopal Padmanabhan Menon, Department of Biochemistry, published Aug. 20, 2004 pp. 274-283.
Planta Med.63(1997) Protectdive Effect of Curcuminoids on Epidermal Skin Cells under Free Oxygen Radical Stress, George Thieme Verlag Stuttgarat, New York.
International Journal of Oncology 24: pp. 321-329, 2004 Effect of curcuma on radiation-induced apoptosis in human cancer cells, Dr. Sarah Baatout.
The Journal of Trauma Injury, Infection, and Critical Care, pp. 927-931 vol. 51, No. 5, Nov. 2001, Protective Effects of Curcumin Against Oxidative Damage on Skin Cells In Vitro: Its Implication for Wound Healing, Toan-Thang Phan, MD, Patrick See, BSc, Seng-Teik Lee, FAMS, FRCS, and Sui-Yung Chan.
Nutrition and Cancer, 44(1), pp. 66-70 2002, Comparative Potencies of Nutraceuticals in Chemically Induced Skin Tumor Prevention, Irene M. Villasenor, Ma Karenina B. Simon, and Ainstein M.A. Villanueva.
Journal of Agricultural and Food Chemistry, J. Agric, Food Chem. 2003, 51, pp. 6604-6611, Comparison of Yield, Composition, and Antioxidant Activity of Turmeric (Curcuma longa L.) Extracts Obtained Using Various Techniques, Mara E. M. Braga, Patricia F. Leal, Joao E. Carvalho, M. Angela A. Meireles.
Alternative Medicince Review: Curcuma longa—Turmeric—Monograph Look Smart Articles, pp. 1-6, Aug. 17, 2005, www.findarticles.com.
OM Organics, Boulder, Colorado—Turmeric: The Ayurvedic Spice of Life, 2003 Prashanti de Jager, pp. 1-8.

(Continued)

*Primary Examiner*—Qiuwen Mi
(74) *Attorney, Agent, or Firm*—Honigman Miller Schwartz & Cohn; Thomas A. Wootton; Jonathon P. O'Brien

(57) ABSTRACT

A topical skin care product is provided that contains therapeutic concentrations of turmeric and other constituents which is colorless upon application to the skin. The product can be used for cosmetic, protective, and healing purposes without staining skin or clothing yellow.

25 Claims, No Drawings

OTHER PUBLICATIONS

The Wall Street Journal , Section D, Aug. 30, 2005, 1 pg article Common Indian Spoce Stirs Hopes, Christina S.N. Lewis.

RD, Sep. 2006 The Miracle Vitamin, Paula Dranov pp. 137-147.

Thesaurus.com,http://thesaurus.reference.com/browse/lotion/, 2007.

The Merck Manual, http://ww.merck.com/mmhe/sec12/ch154a.html, Feb. 2003.

Dictionary.com,http://dictionary.refernce.com/browse/medication, 2006.

* cited by examiner

TOPICAL TURMERIC SKIN CARE PRODUCTS

CROSS REFERENCE TO RELATED APPLICATION

This application is a continuation in part of U.S. application Ser. No. 11/509,212, filed on Aug. 24, 2006 now abandoned, which claims the benefit of U.S. Provisional Application No. 60/713,560 filed Sep. 1, 2005, both applications being incorporated by reference herein in their entirety.

FIELD OF THE INVENTION

This invention relates to the field of topical skin care products containing turmeric. The products have the therapeutic properties of turmeric but without the objectionable characteristics of turmeric.

BACKGROUND OF THE INVENTION

Turmeric and its ingredients have been used for thousands of years because of their therapeutic properties. Topical use of turmeric-containing products has been limited because turmeric has a strong yellow color which stains skin and clothing yellow. Yellow stained skin is simply not acceptable to many people. In addition, the topical application of products containing turmeric in many instances causes yellow staining of a person's clothing. The yellowish appearance of skin caused by the use of turmeric products may last for several days, whereas the yellow staining of clothing may be permanent, ruining the clothing.

The present invention provides a skin care product, for topical application, colorless upon application to the skin, which contains high concentration levels of turmeric while retaining the therapeutic properties of turmeric but without the objectionable staining characteristics described above.

SUMMARY OF THE INVENTION

The present invention provides a neutral composition comprising a therapeutic effective turmeric extract and a neutralizing agent. The turmeric extract contains 0.05% to about 10% of extracted turmeric components. The ratio of turmeric extract to neutralizing agent is from about 1:1 to about 1:20 (turmeric:neutralizing agent), and all ratios between about 1:1 to about 1:20, and in some cases can be as much as 1:40, and all ratios between about 1:20 to about 1:40. The pH value of the neutral composition is in the range of from about 2 to about 5.0. The present invention also provides a skin care product of from 1 to 40% neutral composition in a lotion having a pH of about 1.5 to 7.0.

The neutralizing agent of the present invention comprises at least one extract referred to herein as a "berry" extract and it can be made from any suitable plant such as blueberries, coffee berries, coffee beans, green tea, pomegranates, bilberries, raspberries, black raspberries, cherries, saskatoons, serviceberries, strawberries, chokecherries, huckleberries, buffaloberries, grapes, blue/purple grapes of many varieties, goose berries, bearberries, moonseed berries, mountain currant (ribes novadense), teas, spinach, asparagus, uva ursi, or mixtures thereof. The neutralizing agent optionally further comprises an acidic solution wherein the pH value of the acidic solution is below 6.0.

Specifically, the acidic solution is an organic substance such as lemon oil, lemon juice, orange juice, acetic acid, vinegar or any known organic liquids having a pH value below 5.0.

Specifically, the acidic solution is an organic substance having a pH value in a range from about 1.0 to about 3.0.

Specifically, the acidic solution is a non-toxic inorganic acid solution suitable for use by animals including a human and which has a pH value below 5.0.

Specifically, the acidic solution is of a type suitable for application to a person's skin.

Specifically, the acidic solution is lemon oil, lemon juice or a combination thereof.

The present invention further provides a skin care product comprising the neutral composition and a commercially available lotion such as body lotions or moisturizers; a wound healing product; an allergy relief product; an anti-inflammatory product; an anti-cancer product; a sunscreen product; an anti-aging product; an anti-oxidant product; an osteoporosis product; an osteoporosis product containing vitamin D, of combinations thereof.

Specifically, the neutral composition is in a range from about 1% to about 40%, from about 1% to about 30%, from about 1% to about 20%, or from about 1% to about 10% of the total volume of the skin care product.

Specifically, the neutral composition is about 5% of the total volume of the skin care product.

Specifically, the skin care product has a pH range from about 1.5 to 7.0, from about 3.0 to about 6.5, from about 4.0 to about 6.0, or from about 5.0 to about 6.0.

Specifically, the skin care product has a pH of about 5.5.

The present invention further provides a method of topically applying a skin care product to skin using the compositions herein described. The present invention further provides a method of preventing or treating various skin ailments or diseases using therapeutic amounts of the compositions herein described and applied topically to a patient in need thereof.

The present invention further provides a process for preparing both the neutral composition and the skin care product. The present invention further provides products that are a result of the processes described herein.

DETAILED DESCRIPTION OF THE INVENTION

Definitions

The term "about" means plus or minus 15%.

The term "berry" is any plant material suitable for producing a color neutralizing agent. Examples of berry include, but not limited to, blueberries, coffee berries, coffee beans, green tea, pomegranates, bilberries, raspberries, black raspberries, cherries, saskatoons, serviceberries, strawberries, chokecherries, huckleberries, buffaloberries, grapes, blue/purple grapes of many varieties, goose berries, bearberries, moonseed berries, mountain currant (ribes novadense), teas, spinach, asparagus, uva ursi, or mixtures thereof.

The terms "extract(s)" and "extraction" refer to any method of rendering in liquid form any part of a plant or natural product. The term extract can include the resins from plants. Means to produce extracts and resins can include mashing, grinding, blending, tumbling, stirring and the like. Extraction can optionally involve, but does not require, the use of solvents such as water, acetone, ethanol and isopropanol. Extraction can optionally involve reducing a plant directly into a fine powder form, such as by fine grinding or milling thereby reducing the plant to small particles such as micron or nano sized particles that can be mixed directly into a lotion without the need for the use of traditional solvent based extraction procedures.

The term "lotion" means a solution that is more viscous than water, such as a hand lotion, a cream, an ointment and other forms of moisturizers. Lotions can be applied to the skin from a tube, a pump applicator, a spray device, or related applicators.

The term "neutralizing agent," means the extract made from the berry. In some places herein this term is also known as "neutralizing color."

The term "neutralized turmeric" or "neutralized turmeric base" refers to a composition comprising both turmeric extract and neutralizing agent. Neutralized turmeric is colorless when applied to human skin, including skin with little natural color. Neutralized turmeric can be used by itself, in concentrated or dilute form and it can be combined with other liquids or solutions, such as commercially available creams and lotions.

The term "organic solvent" or "organic solution" is any hydrocarbon based solvent that is also soluble in water. Examples include, but are not limited to, simple alcohols, $C_1$-$C_8$ alcohols, $C_1$-$C_4$ alcohols, such as methanol, ethanol, propanol, isopropanol (IPA), butanol, isobutanol, acetone, DMSO, and the like, either alone or in combination, mixed in any ratio, with or without water. One example of organic solvent is ethanol and isopropanol, with or without acetone and water. Another example of an organic solvent is a mixture of equal amounts of ethanol, isopropyl alcohol (IPA) and acetone.

The term "solution" means any material that can be spread on a surface easily and that contains enough water to measure the solution's pH. A solution may be cloudy or clear, have color or not, be thick and viscous like a heavy cream or thin as water. As used herein, solution does not mean free of precipitates.

The term "turmeric" means any part of any of the plants in the turmeric family. Turmeric is known to contain curcumin and curcuminoids. Turmeric extracts can contain hundreds of compounds, in addition to curcumin and curcuminoids.

The term "turmeric extract" means the extracted components of turmeric, in solution, after extraction with a solvent. The solvent can be water, or water based, an organic solvent, or any combination of common solvents. To make turmeric extract, one starts with whole turmeric plant parts, or dry powdered turmeric, commercially available. The whole turmeric is extracted with solvent and the solid residue left after extraction is discarded. The turmeric extract can be concentrated or dilute. Turmeric "extract" can also be made of whole turmeric plant that is ground an milled to such fine particle size that it can be directly mixed with the solutions and creams of this invention.

General Description

Skin care products of the present invention are solutions and lotions which contain turmeric extract and a color neutralizing agent. The solutions may be used for the treatment of wounds, burns, (including sun burns), and psoriasis. They may be used as or in body lotions, moisturizers, antiseptic agents, beauty aids, allergic reaction formulations, anti-inflammatory products, anti-cancer products, anti-aging products, anti-oxidant products, and osteoporosis products, including the use as a supplement to vitamin D. The skin care products also provide sun and UV light protection and could be given a Sun Protection Factor (SPF) rating or equivalent thereof because they protect the skin from harmful ultraviolet (UV) rays including UVA and UVB.

This invention allows for the use of turmeric and all of its active ingredients, including those with staining properties to be used at any concentrations, but especially at therapeutic levels or amounts or concentrations and thus provide the therapeutic effects and benefits of the turmeric but without unwanted color from those aspects of turmeric which act as a dye to skin and clothes. This dye is a property of turmeric tolerated by some for thousands of years. Now, with the invention disclosed here, for the first time, this chemical turmeric which was also previously a dye, can be used without the yellowing of skin and fabrics. This invention describes examples of turmeric in creams and lotions, all of which would be yellow staining were it not for the color neutralizing effects of the berry solutions described herein.

The therapeutic properties of turmeric are well known, both by ingestion and with topical applications. Previous to this invention however when therapeutic levels of turmeric were used in lotions they were staining. Using the descriptions provided herein topical formulations of turmeric can be prepared at therapeutic levels and used even by people with fair skin with none of the typical staining that comes with turmeric lotions.

Therapeutic levels of turmeric in topical applications will vary depending on the condition to be treated and sensitivity of the patient. One skilled in the art would be able to determine suitable levels for individual patients. A treating physician or skin care specialist will typically start with lower levels and increase to higher levels when it is established that the patient has no adverse reaction. Turmeric has a very good safety record with few known side effects. It is usually extremely well tolerated, except when rejected because of its staining properties. Therapeutic levels of turmeric in lotions will typically range from about 0.5% to 1.5% turmeric extract the final skin care product. See the sections below entitled, "Preparation of the turmeric extract" and "Final products."

The incorporation of turmeric in topical formulations typically results in yellow formulations that give a yellow stain to skin and clothes. Since yellowing of the skin and clothes is objectionable to many people, topical applications of turmeric, especially in the West, are limited. It is possible for a person to ingest turmeric, but adequate skin treatment is difficult to achieve by oral administration of turmeric. This is due to the poor absorption of turmeric and limited concentrations available to the skin from internal use. The present invention discovers a topical lotion containing turmeric at concentrations similar to those used for thousands of years in India and China to provide therapeutic benefits for a wide variety of diseases and ailments, only without the yellow staining, or indeed, without any staining of any color, to the skin or clothes.

The skin care products of the present invention have been show to exhibit, in addition to sun and light protection properties, anti-inflammatory activity for osteoarthritis, relief from psoriasis, and as an anti-infective for treating skin infections associated with acne, wounds and other symptoms of infection.

The skin care products of the present invention can be in any form suitable for topical application and include, but are not limited to, creams, lotions, ointments, spray solutions, and the like.

Turmeric formulated into various solutions, liquids, lotions, creams etc. that no longer have the staining properties of turmeric are referred to herein as, "neutralized turmeric", "color neutralized turmeric" or "neutralized turmeric base."

Traditionally, if a therapeutic effective quantity of turmeric extract is mixed with common lotions, ointments, or the like, the resultant mixture appears yellow. If applied to a person's skin, it will stain the skin and any clothes that contact the skin. Using the procedures described herein, one can now make a turmeric lotion with high levels of turmeric extract that will have an "off white" color (or it can be any color, including blue, tan, brown, pink or other color) but when applied to the skin, surprisingly, it no longer possesses the yellow staining properties of turmeric and turmeric extract. It also doesn't stain skin or clothes with the color from the color neutralizing agent source, the berry, whether it is blueberry, raspberry, grape, tea or any other plant.

Preparation of the Turmeric Extract

Turmeric is available in raw form and as a dry powder. Turmeric can vary in its concentration of active ingredients due to growing conditions and harvesting techniques. It is preferable to use a known source and standard of turmeric. A suitable powder source is McCormick & Co., among others, and a suitable source of turmeric extract is Camden Gray Company, among others. Dry turmeric powder is a suitable starting material.

Turmeric extract may be prepared as follows: a quantity of turmeric powder is weighed and a known weight of such powder is added to a solvent system for the extraction of the active ingredients of the turmeric. Appropriate solvent systems are well known. Turmeric can be extracted using many different solvents, solvent systems and techniques. Water, ethanol and isopropyl are frequently used, either alone or in combination, because they are often allowed by governments to be used in the manufacture of foodstuffs. Techniques for using these and other solvents, including supercritical fluid extraction (SFE), low pressure solvent extraction (LPSE), Soxhlet extraction (Soxhlet), hydrodistillation (HD) and others are known. A good review of a few methods and solvents is available in the Journal of Agriculture and Food Chemistry (2003), Vol 51, pp 660-6611, titled, "Comparison of Yield, Composition and antioxidant Activity of Turmeric (*Curcuma longa* L.) Extracts Obtained Using Various Techniques" by Mara E. M. Braga et al are incorporated by reference herein in their entirety. Additional means of making turmeric extracts are possible and others will be developed. Some nontraditional ways of making an "extract" will likely involve direct micronizing the turmeric plant and producing a fine powder such that most of the active ingredients of the turmeric can directly into solutions and lotions as if a traditional solvent extract was prepared.

The addition of acetone to ethanol and IPA is not required, but it works especially well. Water could also be used. A typical procedure suggested here combines 100 cc of ethanol with 100 cc of isopropyl alcohol and 100 cc of acetone with 30 grams of turmeric powder. However, other procedures and concentrations may be used. In this document the solvent system just described or an equivalent system shall be referred to as an example of an "organic solvent" and one skilled in the art could easily make variations of the ethanol, isopropyl alcohol, acetone examples described here. "Organic solvent" is any solvent that uses any hydrocarbon having water miscible properties and commonly called a solvent or any combination of solvents, such as simple alcohols like methanol, ethanol, propanol, butanol, acetones, and the like, either alone or in combination, mixed in any ratio, an example being a mixture of equal amounts of ethanol, isopropyl alcohol and acetone.

To prepare turmeric extract, whole turmeric or turmeric power (obtained commercially or ground) is extracted. The turmeric extract can vary from 0.5 g/100 cc to 9.5 g/100 cc of extracted turmeric in the solution of the extract, depending on the method of extraction and the type and quality of the whole turmeric used. The concentration may be from 4 to 8 g/100 cc. These amounts can also be described in percent terms. Used here, 1 g of turmeric in 100 cc is 1% turmeric (extracted) in the turmeric extract. It should be understood that the actual concentration of turmeric in the turmeric extract can vary; it can be from 4 to 10%, 4 to 25%, 10 to 15%, 10 to 20%, 9 to 12%, 30 to 40%. In some applications lower amounts may be useful, such as 4 to 8%, 4 to 6% or 6 to 8%, or 6 to 12% turmeric in the extract, or any combination of these percentages. Here, "cc" and "ml" have their common definitions and they mean about the same thing and they are used interchangeably.

Higher concentrations of turmeric extract tend to be unstable and it is recommended that if the turmeric extract is to be stored, its concentration should be 10% or less, which may be stored indefinitely. Stability has been seen for several years.

The neutral compositions are useful either by themselves or to make the final skin care product. See descriptions below under, "Final products" for descriptions of how the turmeric extract can be made into lotions and creams and especially therapeutically effective lotions and creams that are useful for the prevention and treatment of various skin ailments and disorders including sun and light protection, therapy for sunburn, burn relief, anti-inflammatory activity, anti-inflammatory activity for osteoarthritis, relief from psoriasis, and as an anti-infective for treating skin infections, as an anti-infective for treating skin infections associated with acne, wounds and other symptoms of infection, either as prevention or treatment.

The turmeric extract can be made into a lotion and later neutralized or it can remain in the organic solution until neutralization. It is best to neutralize turmeric first, before putting into a lotion for most applications.

Neutralizing Agent from Natural and Synthetic Plant Products and Colors

The neutral composition is made by adding turmeric extract to compositions rich in colored natural plant products. The active ingredient of these natural plant products may vary; it is thought to be various types and forms of natural phytochemicals and some of them may be characterized as anthocyanins and or bioflavonoids. Descriptions of their actual compositions are important only if attempts are made to practice the invention with synthetic, artificial or previously isolated components equivalent to those described herein. Use of such compounds would be routine given this disclosure. Any suggestion as to the chemical structure or name of these phytochemicals should not in any way be used to limit this invention. The practice of the invention does not in any way require chemical structure or formula.

The active components of the neutralizing agent are in those extracts made from the deep colors from plants. Preferred plant sources are those known to be rich in color; the more potent the neutralizing agent, the deeper and darker the plant color. Blueberries, for example, when properly squeezed, crushed, mashed or ground have a lot of neutralizing agent. The neutralizing agent can be any color that is not white or light. It can even be yellow, a color, for example, found in Sasafras. Preferred neutralizing agents are blue, purple, red, black, green and by another name and in any combination or variation.

Surprisingly and unexpectedly, these highly colored materials can be properly combined with a turmeric extract to produce a lotion that is not staining to the skin, nor does it impart any color to the skin or to clothes that contact skin after recent application of the lotions. These highly colored materials, or "neutralizing agents," are frequently staining when used by themselves or when mixed with other neutralizing agents. Surprisingly, the inventive compositions described herein are colorless when applied to the skin but they retain the beneficial properties of lotions or creams that contain turmeric.

The intermediates and final products are themselves not clear; they may have an off-white color, which can range from cloudy to milky blue and even pink, but when applied to the skin, even to fair skin, they are colorless and non-staining. This document refers to extracted plant compositions as "neutralizing agent(s)."

The neutralizing agents neutralize and or mask the distinctive and powerful yellow color from turmeric, without adversely affecting its beneficial properties. The neutralizing agents can be up to 40% of the skin care product. In different aspects of the invention specific disclosure is made of various skin care products containing 1, 5, 10, 15, 20, 25, 30, 35, 40,% neutralizing agent.

Examples of plant materials that can be used to produce such neutralizing agents are: blueberries, coffee berries or beans, green tea, and pomegranates. Other examples of berries that could provide the neutralizing color of this invention are: bilberries, raspberries, black raspberries, cherries, saskatoons, serviceberries, strawberries, chokecherries, huckleberries, buffaloberries, grapes, goose berries, bearberries, moonseed berries, mountain currant (ribes novadense), and blue/purple grapes of many varieties. In addition to numerous types of berries, many plants can be used as well, such as various teas, spinach, asparagus, uva ursi, sassafras and other plants rich in phytochemicals. Most natural berries, many beans, teas and other plants can be used to make the neutralizing agent, all of such plant type materials listed above as well as other suitable plant materials may herein be referred to here as "berry."

Other coloring, natural or synthetic, also may be used without departing from the scope of the invention.

Preparation of the Neutralizing Agent

Each type of starting material will act differently, depending on its level of color in the natural state. For example, blueberries, when ripe, have a very deep dark purple blue color and a high concentration of neutralizing color or neutralizing agent. Their juice can stain skin and clothes due to this rich color. A grape also has neutralizing color; the amount of neutralizing agent of the grape will depend on the variety of the grape, how it was grown and when it was picked. But on average, the juice from most grapes, when compared to the juice from blueberries, is much lower in neutralizing agents, when comparing similar volumes of juice from blueberry vs. grape. Both of these plants, blueberry and grape (and many others, some mentioned above) could be used as the starting material for the neutralizing agent of the invention described herein. But their preparation and how they are mixed would differ because they each have different amounts of neutralizing color in their natural state. However, if one started with large quantities of grape one could easily determine how to extract and use the neutralizing agent, through evaporation, filtration or other known methods. Adjustments in the process can be readily made to accommodate the different concentrations of neutralizing agent present in different amounts in different natural products. The neutralizing agents, when properly prepared, eliminate the staining color of turmeric without reducing its beneficial properties.

Whole berries, such as blueberries, and or their skins, are broken and their juice extracted. This can be done with crushing, grinding, mashing, stirring, shaking, mixing and related methods, some described above, using any assortment of well known mechanical devices to assist the effort. It is preferred that the berries should not be dried before their color is extracted, as more neutralizing agent can be obtained this way. It is possible to use dried and reconstituted berries but avoiding drying the extract makes the neutralizing agent more effective at neutralizing the turmeric extract. Keeping the berry intact and using extracts in liquid form is preferred.

Acid and Heat

In one aspect of the invention, acid is used to increase the yield of neutralizing agent. Any acid can be used. Weak acids are disclosed. Citrus based acids made from lemon, orange or other citrus are disclosed. Orange and grapefruit are other readily obtained alternatives. Acetic acid or vinegar could be used. The acid is added to the berries when they are extracted. In one example, equal parts berry and lemon juice are used. When such an acid is used the pH of the neutralizing agent will be in the range of 2.5 to 3.5. It is important to monitor and adjust the pH as needed. See "pH considerations."

Another method of extracting neutralizing agent from a berry is to heat the berry extract to a level below the boiling temperature of the mixture until the ingredients are thoroughly mixed and warmed. Heating increases the efficiency of the extraction and potency of the neutralizing agent.

The techniques of adding acid, for example in the form of lemon juice, can be combined with heating to obtain maximum neutralizing agent.

Berry Extraction Considerations and Solutions

After the berries are extracted as described above, with or without heat and acid, the solids are removed from the extract to produce the neutralizing agent. Settling, centrifugation, filtration, any number of other procedures can be used to separate the solids from the neutralizing agent. Typically about half the extract will settle but amounts can vary.

pH Considerations

The addition of an acid is used to control and achieve the optimal pH of both the neutralizing agent and the final skin care products.

During berry extraction, the pH of the berry extract is not critical but when the neutralizing agent is later combined with the turmeric extract, the pH of the neutralizing agent may need adjustment in order to make a skin care product of proper pH. pH is important to the look, feel and utility of the skin care product. pH also affects the shelf life of the skin care products. The pH of the skin care product should be between about 1.5 and 7.0, and more preferably between 4.0 and 6.0. A skin care product of pH about 5.5 is described. Basic solutions with a pH over 7.0 can be made but they have a poor shelf life. A high pH can break down turmeric. Turmeric is not very stable in high pH solutions. The pH of the turmeric extracts will be about 3.5 to 4.5.

Processing the Neutralizing Agent

Following the extraction of the berry, the extract is allowed to settle and separate into solid and liquid phases. This separation step can be facilitated by centrifugation, filtration or other known means, or the extracts can just be allowed to sit and precipitate. The solids are removed and discarded. This liquid phase after the solids are removed is called the "neutralizing agent."

Combining the Neutralizing Agent with the Turmeric Extract to Produce the Neutral Composition The turmeric extract is combined, in the proper ratios, with neutralizing agent to achieve the "neutral composition." The proper ratio can be anywhere between and including 1:1 (turmeric extract: neutralizing agent) and up to and including 1:20. Specifically described are ratios of 1:1, 1:2, 1:3, 1:4, 1:5, 1:6, 1:7, 1:8, 1:9, 1:10 1:12, 1:14, 1:16, 1:18, 1:20. The neutral composition can be used either by itself or it can be further combined or diluted with conventional skin creams or lotions.

With further dilution it becomes the "skin care product." For a more stable skin care product it is recommended that the turmeric extract be added to the blueberry/lemon juice/lemon oil solution rather than to the diluting lotion. In some circumstances, if the turmeric is added to the diluting lotion before the berry extract is added, the product will be less stable.

Final Products

The final skin care products will have a good shelf life and be suitable for shipping to and purchase by the consumer. In order to have the best shelf life, the skin care product will have between about 0.01% and 2.4% turmeric extract. This percentage is a measure of the percent of turmeric components in the skin care product where turmeric extract has a range of between about 0.1 g/100 cc or ml and up to about 10 g/100 cc or ml, where these amounts are said to be about 0.1% to 10% extracted turmeric. The amount of neutralizing agent in the skin care product is the amount needed to neutralize the yellow color of the turmeric.

Therapeutic levels of turmeric extract in the final skin care products will typically start at higher levels than the range indicated above. Therapeutic levels of turmeric extract applied topically are usually in the range of about 0.5% to about 1.5%. Therapeutic levels of turmeric can range from about 0.5% up to about 2.0% of turmeric extract in the final product. Specific therapeutic levels of turmeric in the final product are provided here as notional examples of 0.5%, 1.0%, 1.5%, and 2.0% and all ranges between those numbers. An experienced skin care specialist is able to determine optimum levels. Usually it is turmeric at the higher concentrations that are most desired for therapy but are least desired for their staining properties.

The skin care product can have extracted turmeric levels of about 2.0%. Levels of extracted turmeric in the skin care product of between about 2.4 and 3% are also described. For the colorless final products, the following amounts of extracted turmeric are specifically described: 0.01, 0.05, 0.15, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3 and 2.4, all as percent (%) by weight in weight or in volume (wt/wt or wt/vol estimated) of the final product, and any range between any two numbers provided. The numbers in this paragraph may also be written and considered as weight/ weight (w/w) such as 0.001 mg/g, 0.005 mg/g, 0.010 mg/g, 0.015 mg/g, 0.020 mg/g, 0.030 mg/g, 0.040 mg/g etc. Using a weight of active extracted turmeric as a percent of the total weight.

The skin care products can be made into or added to other topical lotions, creams, or sprayable solutions, including moisturizers.

Neutral Compositions

Neutral compositions have been evaluated in the following ratios. From about 0.5 cc to 4.0 cc turmeric extract mixed with about 10 cc of blueberry lemon juice extract where this extract is made in about equal parts blueberry and lemon juice. When lower amounts of turmeric are used, typically 2 cc turmeric to 10 cc of blueberry lemon juice extract, the mixtures are stable for long periods of time and non-staining. When higher amounts of turmeric are used, over 2.5 cc of turmeric extract and 10 cc neutralizing agent, the mixtures can become unstable after a certain period of time and the yellow tint of turmeric may eventually reappear. Preferably solutions are diluted to, or use less than, 2.5 cc turmeric extract with 10 cc of neutralizing agent.

When the turmeric extract is combined with neutralizing agent and made into a colorless cream, it is preferred that the turmeric extract (typically at 6 to 7 percent turmeric) be combined with about three times as much neutralizing agent as turmeric extract (v/v). Specifically disclosed is 3 cc of turmeric extract to 9 cc of neutralizing agent (ratio of 1:3). For stable solutions the concentration of turmeric in the final product should be reduced as indicated above, to levels of 2.5% or less. Levels of turmeric from 0.1% to 10% (g extracted turmeric/cc) can and have been used prior to neutralization.

Wide variations are possible in the amounts and types of turmeric and a wide variety of plants and berries can be used to make the turmeric extract and the neutralizing agent. Because of the varying nature of the natural products used, a simple test has been devised a simple test to determine when the turmeric extract is neutralized.

Turmeric Neutralization Test

To the turmeric extract which is yellow, neutralizing agent is added and mixed well. The pH is adjusted. Samples are removed and applied to pale skin that is not normally exposed to high levels of sunlight, such as the upper arm, under the ribs or groin.

The samples are rubbed gently into the skin. A white gauze is applied for at least 30 minutes. The gauze is removed and inspected. If the gauze appears yellow, then either the turmeric extract is too strong or the neutralizing agent is too little. Corrections should be made. If the yellow color appears then either additional neutralizing agent should be added, or less or weaker turmeric extract should be used.

DETAILED DESCRIPTION OF THE INVENTION BY NUMBERS

1. A neutral composition comprising turmeric extract and neutralizing agent in a ratio of turmeric extract to neutralizing agent from about 1:1 to about 1:20 (turmeric extract: neutralizing agent).
2. The neutral composition of number 1 wherein said neutral composition has a pH between about 2.0 to about 5.0.
3. The neutral composition of number 2 wherein said turmeric extract contains 0.05% to about 10% of extracted turmeric components.
4. The neutral composition of number 1 further comprising an acidic solution wherein the pH value of the acidic solution is below 6.0.
5. The neutral composition of number 4 wherein said acidic solution is a weak acid.
6. The neutral composition of number 5 wherein said weak acid is lemon oil, lemon juice, orange juice, acetic acid, or vinegar having a pH below 5.0.
7. The neutral composition of number 5 wherein said weak acid is lemon oil or lemon juice, having a pH from about 1.0 to about 3.0 and the neutralizing agent is made from blueberry.
8. A skin care product comprising from about 1 to 40% neutral composition in a lotion having a pH from about 1.5 to 7.0, wherein said neutral composition comprises turmeric extract and neutralizing agent in a ratio of turmeric extract to neutralizing agent from about 1:1 to about 1:20; wherein said neutral composition has a pH from about 2.0 to about 5.0; wherein said turmeric extract contains 0.05% to about 10% of extracted turmeric components; wherein said neutralizing agent comprises at least one extract that is a berry extract, made from any suitable plant.
9. The skin care product of number 8 wherein said berry is any of the following: blueberries, coffee berries, coffee beans, green tea, pomegranates, bilberries, raspberries, black raspberries, cherries, saskatoons, serviceberries, strawberries, chokecherries, huckleberries, buffaloberries, grapes, blue/purple grapes of many varieties, goose berries, bearberries, moonseed berries, mountain currant (ribes novadense), teas, spinach, asparagus, uva ursi, or mixture thereof.

10. The skin care product of number 9 where said berry is a blueberry.

11. The skin care product of number 9 wherein said skin care product comprises said neutral composition and said lotion comprises any commercially available lotions, body lotions or moisturizers.

12. The skin care product of number 9 wherein said skin care product comprises a neutral composition from about 1% to about 30% of the total volume of the skin care product.

13. The skin care product of number 9 wherein said skin care product comprises a neutral composition from about 1% to about 20% of the total volume of the skin care product.

14. The skin care product of number 9 wherein said skin care product comprises a neutral composition from about 1% to about 10% of the total volume of the skin care product.

15. The skin care product of number 9 wherein said skin care product comprises a neutral composition about 5% of the total volume of the skin care product.

16. The skin care product of number 9 wherein said skin care product has a pH range from about 3.0 to about 6.5.

17. The skin care product of number 9 wherein said skin care product has a pH range from about 4.0 to about 6.5.

18. The skin care product of number 9 wherein said skin care product has a pH range from about 5.0 to about 6.0.

19. The skin care product of number 9 wherein said skin care product has a pH range of about 5.5.

20. The skin care product of number 9 wherein said skin care product is incorporated in an ointment, a lotion, a cream or made as a spray solution, that contains therapeutic amounts of turmeric and is applied to a patient in need thereof and may be characterized as any of the following agents: an antiseptic agent; a beauty aid to prevent aging; a wound healing product; an allergy relief product; an anti-inflammatory product; an anti-cancer product; a sunscreen product; an anti-aging product; an anti-oxidant product; a product that treats osteoporosis, and a product that treats osteoporosis in combination with vitamin D.

21. A method of treating a patient in need thereof with a final skin care product comprising a therapeutic amount of turmeric extract, which is applied to the skin of said patient for the prevention or treatment of any of the following ailments or diseases: infections, skin infections, age related skin disorders, sun and age spots, wrinkles and the like, wounds, abrasions in the skin, allergic reactions, inflammation, sores, cancer, keratomas, skin cancer, burns, sun burns, oxidizing injury, osteoporosis, vitamin D deficiency, and combinations thereof; wherein said composition comprises from about 1 to 40% neutral composition in a lotion having a pH from about 6.0 to 7.0, wherein said neutral composition comprises turmeric extract and neutralizing agent in a ratio of turmeric extract to neutralizing agent from about 1:1 to about 1:20; wherein said neutral composition has a pH from about 2.0 to about 5.0; wherein said turmeric extract contains 0.05% to about 10% of extracted turmeric components; wherein said neutralizing agent comprises at least one extract that is a berry extract, made from any suitable plant.

22. The method of treatment of number 21, wherein the therapeutic amount of turmeric extract to be applied is in the range from about 0.5 to 2.0% turmeric extract.

23. The method of treatment of number 22, wherein the therapeutic amount of turmeric extract to be applied is in range from about 0.5 to 1.5% turmeric extract.

24. The method of treatment of number 22, wherein the neutralizing agent is made from blueberry extract.

25. The method of treatment of number 24, wherein said neutralizing agent is made from blueberry extract.

26. A method of preparing a neutral composition comprising: a) mixing powdered turmeric in a water or organic solution; b) extracting the soluble turmeric into a turmeric extract of between about 1 and 40% turmeric and discarding any precipitated solids; c) neutralizing the color of the turmeric extract by adding a neutralizing agent made from: 1) a berry mixed or ground to produce an extract; 2) separating said berry extract into liquid and solid portions; 3) discarding said solid portion; and 4) combining said liquid berry extract with said turmeric extract.

27. The method of number 26 where said berry is blueberry.

28. A method of preparing a skin care product comprising a neutral composition made according to number 22 and diluting said neutral composition with a suitable skin lotion or cream such that the neutral composition comprises from about 1 to 40% of the final skin care product.

29. The method of number 28 wherein said berry is blueberry.

30. A composition made by the process of: a) mixing powdered turmeric in an organic solution; b) extracting the soluble turmeric into a turmeric extract; c) mixing said soluble turmeric extract with a neutralizing agent; wherein said neutralizing agent is made by; 1) grinding, mashing, crushing or mixing a berry to produce an extract; 2) separating said extract into liquid and solid portions; 3) discarding the solid portion and using said liquid portion as neutralizing agent; 4) adding said neutralizing agent and mixing with said turmeric extract to producing a neutral composition.

31. A composition of number 30 wherein said berry is blueberry.

32. A composition of number 31 further comprising any known skin lotions such that the amount of the neutral composition comprises from 1 to 40% of the final skin care product and the known lotions comprise from 99 to 60% of the skin care product.

EXAMPLES

Examples are intended to illustrate rather than define or limit the invention.

In the first example below, the invention is illustrated with a description of a blueberry-turmeric mixture, but any natural source for the neutralizing color could be used. In all of these examples the solutions would be yellow staining, were it not for the neutralizing agent.

The blueberry/lemon juice/lemon oil solution, when prepared as described above, has the color standard of fresh blueberry juice or blueberry jam. If the color is not up to standard, which can occur with long standing or aging, then it will not have as much neutralizing power. This problem can be corrected with the addition of freeze dried blueberry. Such compositions are commercially available, for example see, "Freeze Dried Blueberry Powder Form, Van Drummed Farms, 300 West Sixth Street, Momence, Ill. 60954. The addition of freeze dried blueberry materials will also produce additional pink to purple color. Other blueberry products could also be used but it is recommended that the sugar concentration be kept low to avoid a sticky feel to the lotion.

Drum and air dried blueberries generally cannot be used to produce the neutralizing agent unless they are further treated to reactivate the berry extract after the berries are dried.

Example 1

A mortar and pestle is used to grind 30 grams of turmeric into a fine powder.

A solution of organic solvent comprising 100 cc ethanol, 100 cc of isopropyl alcohol, and 100 cc of acetone is prepared. The 30 grams of fine turmeric powder is added to the organic solution.

The turmeric is mixed well with the organic solution and then allowed to settle. After 72 hours, the solids have separated from the solution and are discarded. The solution of turmeric in the organic solution is removed and called the turmeric extract. The turmeric extract, pH about 4.5, is set aside until the neutralizing agent is ready.

The neutralizing agent is prepared. A batch of raw blueberries are mixed, crushed and ground to produce the neutralizing agent. About equal amounts of blueberry and lemon juice (standard commercial strength) with a pH of about 2.3 to 3.0, are mixed together. About 300 ml of each, blueberry and lemon juice, are mixed and then heated to about 190 degrees F. The blueberries-lemon juice solution is then allowed to cool and settle to slightly above ambient temperature. The pH of this solution is about 2.5 to 3.5. Any solids found in the solutions are discarded; the remaining solution is the neutralizing agent. In the examples below this solution is referred to as "blueberry/lemon juice/lemon oil."

The turmeric extract, 300 ml, pH about 4.5, is then added to the blueberry lemon solutions. After mixing this is called the neutral composition, about 900 ml. in this example. In this example the turmeric extract was about 7% turmeric in the extract. The amount of turmeric extracts in the neutralized base is calculated to be about 2.3%, and its pH is about 4.5. The blueberry extract made as described (with heat and lemon juice) has enough neutralizing strength to neutralize the color of the turmeric. A sample should be tested as above to ensure color neutralization is complete.

The resulting solution, the neutral composition, provides an adequate therapeutic concentration of the turmeric active ingredients for topical use without the yellow staining characteristics of standard turmeric extracts.

If desired, the neutral composition may be incorporated into an ointment base which accepts a liquid solution. For example, 10 grams of an ointment base, such as a hydrophilic absorption base available under the trademark AQUAPHOR from Biersdof, Inc., will accept an equal amount of fluid or approximately 10 cc of the above mixture. In this example the final concentration of turmeric in the skin care product would be about 1.15% and it should have excellent self life. Instead of incorporating the neutral composition in the ointment base described, it could be added to other topical lotions, creams, or sprayable solutions, including moisturizers. Examples 2-9 below describe other lotions that have been made.

Examples 2-9

Following the procedures outlined above for Example 1, the following specific lotions are described. For examples 2-9 when the term blueberry/lemon juice/lemon oil is used it refers to the process described above where 50% blueberry neutralizing agent is made from extracts of 50% blueberry and 50% lemon juice and lemon oil mixed with heating to below the boiling point of the solution, followed by settling and discarding of the solids. See above. When one lotion is said to be comparable to another it means either lotion could be used with a similar results.

Example 2

Use 9 cc of blueberry/lemon juice/lemon oil, as described in example 1; add 1 cc turmeric extract to make a neutral composition. To the neutral composition, add 100 g of "Lubriderm Skin Nourishing—Moisturizing Lotion," Johnson and Johnson, CCI 2007 #730922. The resulting skin care product is light pink to creamy white. It doesn't color the skin and it appears colorless when applied to the skin.

Example 3

Use 5 cc of blueberry/lemon juice/lemon oil, as described in example 1, add 5 cc turmeric extract to make a neutral composition. To this neutral composition, add 100 g of "Lubriderm Skin Nourishing—Moisturizing Lotion," Johnson and Johnson, CCI 2007 #730922. The resulting skin care product is yellow. It doesn't color the skin and it appears colorless when applied to the skin.

Example 3b

Use Example 3, only use 15 cc of blueberry/lemon juice/lemon oil. The resulting neutral composition is tan colored. It does not stain or color the skin. It doesn't color the skin and the skin care product appears colorless when applied to the skin.

Example 4

Use 10 cc of blueberry/lemon juice/lemon oil and 4 cc of turmeric extract to make a neutral composition. To the neutral composition add 100 g of "Lubriderm Skin Nourishing—Moisturizing Lotion," Johnson and Johnson. The resulting skin care product is tan colored and it is free of staining properties. It doesn't color the skin and it appears colorless when applied to the skin.

Example 5

Use 10 cc of blueberry/lemon juice/lemon oil and 4 cc of turmeric extract to make a neutral composition. To this neutral composition, add 100 g of "Jergens Ultra Healing—Heals & Softens," Distributed by Koa Brands Company, Tm.Off. #11583-0-301 Lot #X009225ZZ. The resulting skin care product has a pleasing dark pink color. There is no yellow color or staining properties of the skin care product. It doesn't color the skin and it appears colorless when applied to the skin.

Example 6

Use 10 cc of blueberry/lemon juice/lemon oil and 2 cc of turmeric extract to make a neutral composition. To this neutral composition, add 100 g of "Jergens Ultra Healing—Heals & Softens," as in Example 5. The resulting skin care product has a light pink color, with no staining properties. It doesn't color the skin and it appears colorless when applied to the skin.

Example 7

Use 10 cc of blueberry/lemon juice/lemon oil and 2 cc of turmeric extract to make a neutral composition. To this neutral composition, add 100 g of "Walgreens Complete Moisture Dry Skin Lotion," Distributed by Walgreen Co, Deerfield, Ill. 60015 Item #512505 (This Walgreens lotion is comparable to Vaseline Intensive Care by Chesbrough-Ponds USA.) The resulting skin care product is a pink lotion with no staining properties and is colorless when applied to the skin.

Example 8

Use 8 cc of blueberry/lemon juice/lemon oil and 2 cc of turmeric extract to make a neutral composition. To neutral composition, add 100 g of "Equate-Advanced Healing Lotion—Hydrates & Heals Dry Skin and Skin Protectant," Distributed by Wal-Mart Stores, Inc. Bentonville, Ariz. 72716. (This Wal-Mart lotion is comparable to Vaseline Intensive Care by Chesbrough-Ponds USA.) The resulting skin care product is pink and without staining properties. With time, after several years, if stored at 60 to 72 degrees F, if stored in a 2 oz plastic bottle, this lotion will turn brown or tan but it will not stain the skin or clothes and is colorless when applied to the skin. Even with the passage of time the product retains its cosmetically appealing appearance.

Example 9

Use 8 cc of blueberry/lemon juice/lemon oil and 2 cc of turmeric extract to make a neutral composition. To this neutral composition, add 100 g "Equate-Ultra Strength Lotion-Fast Acting For Long Term Relief of Extra Dry Skin," Distributed by Wal-Mart Stores, Inc., Bentonville, Ariz. 72716. (This lotion is comparable to Jergens Skincare Ultra Healing Lotion from The Andrew Jergens Co.) The resulting skin care product is a pink lotion, without staining properties. After several years, if stored at 60 to 72 degrees F, if stored in plastic bottles, it can turn into a dark pink to red lotion that is also without staining properties and is colorless when applied to the skin. Even after the passage of time the product retains its cosmetically appealing characteristics.

I claim:

1. A process of preparing a non-staining composition, wherein said composition has a pH between 4.0 and 6.0 and contains 0.1 to 2.4% turmeric (w/v), said process comprising mixing a turmeric extract with a berry extract in a ratio from 1:1 parts to 1:20 parts (v/v),
   wherein said turmeric extract is made by:
   1) exposing turmeric to a solvent, until said solvent contains between 0.1 to 10 g turmeric per 100 ml solvent, wherein said solvent is comprised of water, an organic solvent, or a mixture thereof;
   2) separating turmeric residues from the turmeric in solvent, leaving a turmeric extract,
   wherein said berry extract is made by:
   1) selecting a berry that is intact and whole, with a blue, purple, red or black color;
   2) mixing the berry with an acid to form a mixture of berry residues and a liquid, wherein said mixture has a pH between 2.5 and 3.5;
   3) separating the berry residues from the liquid, leaving a berry extract.

2. A process of claim 1, wherein said composition has a pH between 5.0 and 6.0.

3. A process of claim 1, wherein said composition contains about 0.5% to 2.0% turmeric.

4. A process of claim 3, wherein said composition contains about 1.0% turmeric.

5. A process of claim 3, wherein said composition contains about 1.5% turmeric.

6. A process of claim 3, wherein said composition contains about 2.0% turmeric.

7. A process of claim 3, wherein said pH of the composition is about 5.5.

8. A process of claim 3, wherein said berry is blue, purple or black.

9. A process of claim 8, wherein said berry is a blueberry.

10. A process of claim 8, wherein said berry is a grape.

11. A process of claim 1, wherein said turmeric extract to said berry extract is in a ratio from about 1 part turmeric extract to about 3 parts berry extract.

12. A process of claim 1, wherein said turmeric extract to said berry extract is in a ratio from about 1 part turmeric extract to about 5 parts berry extract.

13. A non-staining composition having a pH between 4.0 and 6.0 and containing 0.1 to 2.4% turmeric (w/v), wherein said composition is made by mixing a turmeric extract with a berry extract in a ratio from 1:1 parts to 1:20 parts (v/v),
    wherein said turmeric extract is made by:
    1) exposing turmeric to a solvent, until said solvent contains between 0.1 to 10 g turmeric per 100 ml solvent, wherein said solvent is comprised of water, an organic solvent, or a mixture thereof;
    2) separating turmeric residues from the turmeric in solvent, leaving a turmeric extract, wherein said berry extract is made by:
    1) selecting a berry that is intact and whole, with a blue, purple, red or black color;
    2) mixing the berry with an acid to form a mixture of berry residues and a liquid, wherein said mixture has a pH between 2.5 and 3.5;
    3) separating the berry residues from the liquid, leaving a berry extract.

14. A composition of claim 13, wherein said composition has a pH between 5.0 and 6.0.

15. A composition of claim 14, wherein said composition contains about 0.5% to 2.0% turmeric.

16. A composition of claim 15, wherein said composition contains about 0.5% turmeric.

17. A composition of claim 15, wherein said composition contains about 1.0% turmeric.

18. A composition of claim 15, wherein said composition contains about 1.5% turmeric.

19. A composition of claim 15, wherein said composition contains about 2.0% turmeric.

20. A composition of claim 15, wherein said pH of the composition is about 5.5.

21. A composition of claim 15, wherein said berry is blue, purple or black.

22. A composition of claim 21, wherein said berry is a blueberry.

23. A composition of claim 21, wherein said berry is a grape.

24. A composition of claim 15, wherein said turmeric extract to said berry extract is in a ratio from about 1 part turmeric extract to about 3 parts berry extract.

25. A composition of claim 15, wherein said turmeric extract to said berry extract is in a ratio from about 1 part turmeric extract to about 5 parts berry extract.

* * * * *